United States Patent
Gonzalez et al.

(10) Patent No.: US 8,691,552 B2
(45) Date of Patent: Apr. 8, 2014

(54) MICROAEROBIC CULTURES FOR CONVERTING GLYCEROL TO CHEMICALS

(75) Inventors: Ramon Gonzalez, Houston, TX (US); Paul Campbell, Houston, TX (US)

(73) Assignees: William Marsh Rice University, Houston, TX (US); Glycos Biotechnologies, Inc., Houston, TX (US)

( * ) Notice: Subject to any disclaimer, the term of this patent is extended or adjusted under 35 U.S.C. 154(b) by 183 days.

(21) Appl. No.: 13/126,499

(22) PCT Filed: Oct. 28, 2009

(86) PCT No.: PCT/US2009/062440
§ 371 (c)(1),
(2), (4) Date: Jun. 21, 2011

(87) PCT Pub. No.: WO2010/051324
PCT Pub. Date: May 6, 2010

(65) Prior Publication Data
US 2011/0250654 A1   Oct. 13, 2011

Related U.S. Application Data

(60) Provisional application No. 61/109,018, filed on Oct. 28, 2008.

(51) Int. Cl.
*C12N 1/20* (2006.01)
(52) U.S. Cl.
USPC ........................................................ 435/252.1
(58) Field of Classification Search
None
See application file for complete search history.

(56) References Cited

U.S. PATENT DOCUMENTS

| | | |
|---|---|---|
| 2007/0048849 A1 | 3/2007 | Laffend et al. |
| 2008/0199926 A1 | 8/2008 | Burgard et al. |

FOREIGN PATENT DOCUMENTS

| | | |
|---|---|---|
| EP | 09824100.3 | 8/2011 |
| WO | WO2007115228 | 10/2007 |
| WO | WO2010051324 | 5/2010 |

OTHER PUBLICATIONS

Altaras et al., "Enhanced Production of (R)-1,2-Propanediol by Metabolically Engineered *Escherichia coli*", Biotechnol. Prog., 16: 940-946 (2000).*
Bouvet et al., "Taxonomic diversity of anaerobic glycerol dissimilation in the Enterobacteriaceae", Res. Microbiol., 146: 279-290 (1995).*
Daniel et al.,"Biochemical and Molecular Characterization of the Oxidative Branch of Glycerol Utilization by *Citrobacter freundii*", Journal of Bacteriology, 177(15): 4392-4401 (1995).*
Yazdani et al: "Engineering *Escherichia coli* for the efficient conversion of glycerol to ethanol and co-products"; Metabolic Engineering; vol. 10~ Sep. 9, 2008; pp. 340-351; XP025800636.
Gonzalez et al: "A new model for the anaerobic fermentation of glycerol in enteric bacteria: Trunk and auxiliary pathways in *Escherichia coli*". Metabolic Engineering. vol. 10. May 27, 2008. pp. 234-245. XP024525627.
Durnin et al: "Understanding and 1-9 harnessing the microaerobic metabolism of glycerol in *Escherichia coli*". 1 Biotechnology and Bioengineering, vol. 103. Dec. 30, 2008. pp. 148-161. XP002671094.

\* cited by examiner

*Primary Examiner* — Anand Desai
(74) *Attorney, Agent, or Firm* — Boulware & Valoir

(57) ABSTRACT

Glycerol or other reduced carbon sources may be used as a feedstock for the microbial production of chemical products under certain microaerobic conditions. For example, such production may occur under microaerobic or microrespiratory conditions in which electron acceptors are consumed in the reaction as quickly as they are added. In such reactions, the reaction product is at least as reduced as carbon source. Further, during such a reaction, at least some of the carbon source is used to generate cell mass. In addition, microorganisms with modified genomes are provided for carrying out the methods herein.

7 Claims, 12 Drawing Sheets

MICROAEROBIC CULTURES FOR CONVERTING GLYCEROL TO CHEMICALS

CROSS-REFERENCE TO RELATED APPLICATIONS

This application claims priority to U.S. Provisional Application No. 61/109,018, filed Oct. 28, 2008 and incorporated herein by reference.

STATEMENT REGARDING FEDERALLY SPONSORED RESEARCH

This invention was made with government support under Grant Number CBET-0645188 awarded by the National Science Foundation and under Grant Number 2005-35504-16698 awarded by the United States Department of Agriculture. The government has certain rights in the invention.

BACKGROUND OF THE INVENTION

In recent years, there has been a significant increase in the production and use of biofuels, such as biodiesel and bioethanol, generally produced by transesterification using vegetable oils or animal fats and an alcohol. A byproduct of this reaction is glycerol, and there is currently a surplus of waste glycerol produced in biofuel plants.

Glycerol is a viscous liquid that is difficult to process, and it is generally disposed of by incineration or chemical processing. However, such strategies negate the positive environmental impact of using biodiesel fuels. For example, incineration of glycerol may release pollutants into the air. Rather than disposing of the glycerol, it would be better to process the glycerol into another chemically useful product.

Glycerol can be used as a feedstock in biological conversion, a process in which a microorganism enzymatically converts glycerol into specific chemical products, such as ethanol or lactic acid. Conversion of glycerol to ethanol or other products is advantageous because they have value as fuel or as feedstocks for other processes.

Anaerobic fermentation and aerobic respiration have been used for the industrial production of chemicals, and are the two methods applied to date for glycerol-based cultures. Oxygen rich respiration offers very efficient cell growth (growth rate and yield) and converts a high percentage of the carbon source into carbon dioxide and cell mass (see table below). Anaerobic fermentation, on the other hand, results in poor cell growth, but the synthesis of several fermentation products at high yields (e.g. lactate, formate, ethanol, propionate, succinate, etc.).

| Respiratory vs Fermentative Metabolism | | | |
|---|---|---|---|
| Variable | Anaerobic Fermentation | Anaerobic Respiration | Aerobic Respiration |
| Growth Rate | LOW | Intermediate | HIGH |
| Cell Mass | LOW | Intermediate | HIGH |
| Product Yields | HIGH | High/Intermediate | LOW |
| Capital Cost | LOW | LOW | HIGH |
| Energy Input | LOW | LOW | HIGH |

Producing chemicals via oxygen rich processes, however, is more costly than using anaerobic methods for two reasons. First, aerobic fermenters are more expensive to build, due to both the higher cost per unit and the need for smaller fermenters with reduced economy of scale. Secondly, the aerobic fermenters are more costly to operate than their anaerobic counterparts due to low solubility of oxygen, which in turn requires high energy input to ensure appropriate supply of oxygen to the cells. This is especially relevant for the production of commodity chemicals, where fermentation costs can represent 50-90% of the total production cost.

Therefore, anaerobic methods are usually preferred where possible, and it is typical to grow cells to a large number aerobically, and then switch the cells to anaerobic culture for the production of desired molecules. Recently, another anaerobic method has been developed to biologically ferment glycerol into ethanol and other chemicals under anaerobic conditions. This method is described in co-pending WO2007115228, incorporated herein by reference in its entirety for all purposes. While an advantage of anaerobic fermentation of glycerol is the increased percentage yield of the desired end product, a disadvantage is slower bacterial growth associated with the lack of oxygen in the system. Thus, again what is needed in the art is a better system of culturing bacteria, using glycerol as a feedstock to produce high yields.

SUMMARY OF THE INVENTION

We provide herein a method of growing bacteria under microaerobic conditions that improves the yield of anaerobic cultures, yet is less costly than aerobic fermentations, using low but measurable oxygen, and sufficient to maintain redox balance, which we call "microaerobic." Using glycerol as a feedstock, bacteria are grown under low oxygen conditions, but with a small amount of oxygen or other electron acceptor such as nitrate or nitrite, so that ultimately the redox balance for the conversion of the substrate into the product in a stoichiometrically defined pathway is equal to or greater than zero and a fraction of the substrate is used to generate cell mass.

By "microaerobic" what is meant is 1-20 mg $O_2$/L/h or its equivalent. Preferably 2-15 $O_2$/L/h is used, and more preferably 3-10 or 5 mg $O_2$/L/h.

In addition to variations in the inlet gas flow rate or the composition of the inlet gas, microaerobic conditions can also be produced by decreasing the stir rate (thus decreasing the oxygenation of a large culture), or by adding more feedstock to increase the cell density (and hence higher oxygen demand), or combinations thereof.

By "deletion" ("Δ") or "disruption" what is meant is that a gene or protein is changed such that only 10% of the activity of an appropriate control strain is retained. Preferably no detectable activity is retained. Genes can be partially or completely deleted, or interrupted with stop codons, or mutated so as to yield an inactive protein product. Proteins can also be inactivated with inhibitors or by suppression of expression or translation, and the like.

By "overexpression" what is meant is that a gene or protein is changed so as to result in at least 150% activity as compared with an appropriate control strain. Preferably as much as 2, 5 or 10 fold increases in activity are obtained. Overexpression can be achieved by mutating the protein to produce a more active form or a form that is resistant to inhibition, by removing inhibitors, or adding activators, and the like. Overexpression can also be achieved by removing repressors, adding multiple copies of the gene to the cell, or upregulating the endogenous gene, and the like.

There is provided a method for producing a chemical product in a microorganism that includes providing conditions to produce the product, wherein the degree of reduction balance for the conversion of the substrate into the product in a stoichiometrically defined pathway is equal to or greater than zero, the degree of reduction balance for the conversion of the substrate into cell mass is greater than zero, and a fraction of the substrate is used to generate cell mass. In addition, the degree of reduction balance for the conversion of the substrate into cell mass is greater than zero.

The chemical product so produced can be, but is not limited to, lactate, ethanol, and succinate.

DETAILED DESCRIPTION OF THE INVENTION

Figure 1:
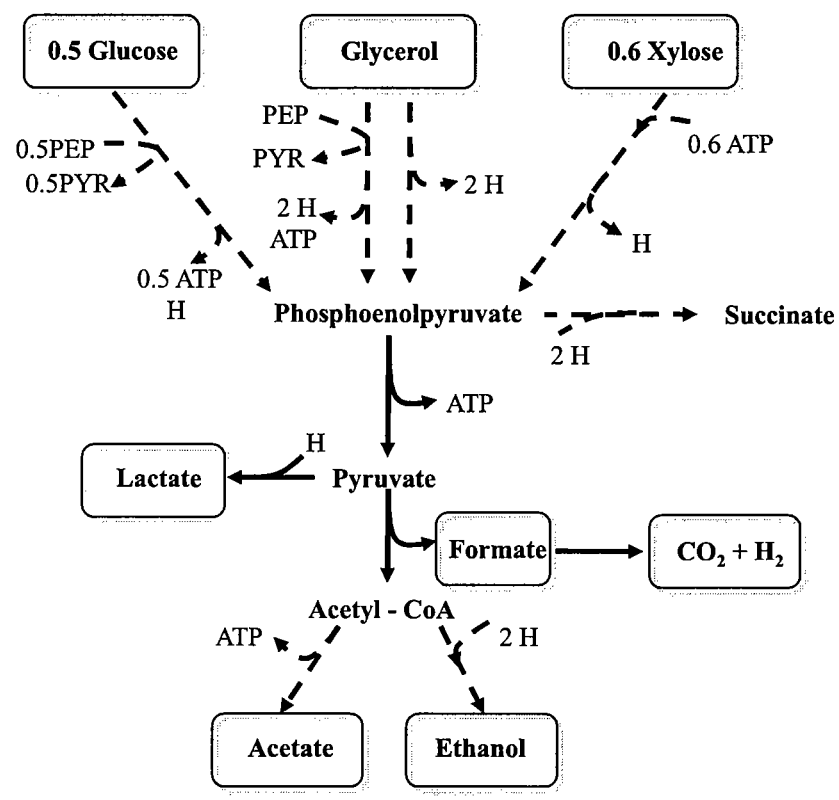
FIG. 1 illustrates the production of reducing equivalents generated by the metabolism of glucose, xylose, or glycerol to produce succinate, ethanol, lactate, and acetate in accordance with the present techniques.
Figure 2:
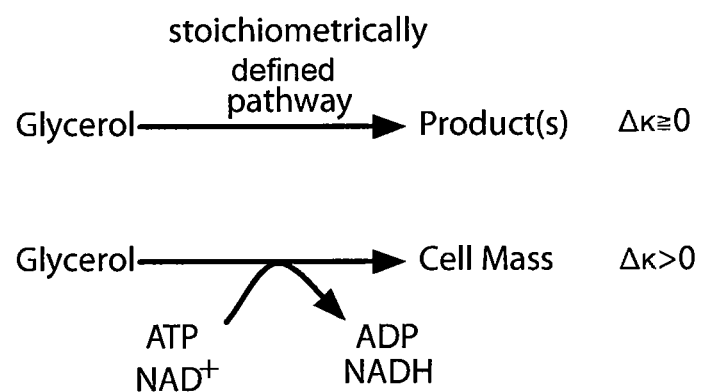
FIG. 2 illustrates the relationship between glycerol, chemical products produced from glycerol, and cell mass; and the net production of reducing equivalents in accordance with the present techniques.

The synthesis of microbial cell mass from certain carbon sources may be harnessed under the appropriate conditions to produce a useful chemical product. The microbial synthesis of cell mass from carbon sources that are more reduced than biomass, such as glycerol, is a metabolic process that results in the net generation of reducing equivalents. Under reaction conditions in which there are substantially no electron acceptors available (e.g. under micro-respiratory or micro-aerobic conditions), conversion of some of the feedstock into a reduced product allows the reaction to maintain redox balance. The activity of this conversion to a reduced product facilitates attaining redox balance by consuming the excess reducing equivalents generated in the synthesis of cell mass from the carbon source. In many instances, a redox-balanced system allows for increased microbial growth, which in turn allows the reaction to produce increased amounts of the desired chemical product.

The present techniques may release redox constraints imposed by the incorporation of carbon sources into cellular biomass, a metabolic process that results in the generation of reducing equivalents when the carbon sources are more reduced than the biomass. For example, the low levels of oxygen available under microaerobic conditions may serve as a sink for the excess reducing equivalents, thus improving the redox balance, allowing the incorporation of a larger fraction of glycerol into cell mass, and generating additional ATP. In the present context, the terms "biomass" or "cell mass" relate to the amount of a given cell culture, i.e. any organism or living cell growing in a medium, that is actively growing. In general, the cell mass yield of a cell culture may be measured as gram cell mass obtained per liter of culture medium.

It is envisioned that the present techniques may be useful for the production of any suitable product wherein the degree of reduction balance for the conversion of the carbon source into the chemical product is equal to or greater than zero, i.e., the conversion of glycerol into the chemical product does not consume more reducing equivalents than it produces. Such products may include alcohols, alcohol derivatives, sugar alcohols (e.g. ethanol, propanol, butanol, butanediol, arabitol, xylitol), organic acids (e.g. formate, succinate, propionate, fumarate, malate, lactate, propionate, pyruvate), amino acids (e.g. alanine, asparagine, aspartic acid), or lactones (e.g. gamma-butyrolactone, caprolactone/lactone).

TABLE 1

Analysis of redox balance for the conversion of glycerol into cell mass and selected products. In all cases, the products are synthesized through a redox-neutral or redox-generating pathway.

| Pathway | Stoichiometry[a] ($\kappa$[b]) | $\Delta\kappa$[c] (H[d]) |
|---|---|---|
| glycerol→cell mass | $C_3H_8O_3$ (14/3)→$3CH_{1.9}O_{0.5}N_{0.2}$(4.3)[e] | 1.1 (0.55H) |
| glycerol→ethanol + formate[f] | $C_3H_8O_3$ (14/3)→$C_2H_6O(6) + CH_2O_2(2)$ | 0 (0H) |
| glycerol→succinate | $C_3H_8O_3(14/3) + CO_2(0)$→$C_4H_6O_4(14/4)$ | 0 (0H) |
| glycerol→propionate | $C_3H_8O_3$ (14/3)→$C_3H_6O_2(14/3)$ | 0 (0H) |

TABLE 1-continued

Analysis of redox balance for the conversion of glycerol into cell mass and selected products. In all cases, the products are synthesized through a redox-neutral or redox-generating pathway.

| Pathway | Stoichiometry$^a$ ($\kappa^b$) | $\Delta\kappa^c$ (H$^d$) |
|---|---|---|
| glycerol→lactate | $C_3H_8O_3$ (14/3)→$C_3H_6O_3$(12/3) | 2 (1H) |
| glycerol→alanine | $C_3H_8O_3$(14/3)→$C_3H_7NO_2$(12/3) | 2 (1H) |

$^a$Pathway stoichiometry accounts only for carbon balance between reactants and products.
$^b$The degree of reduction per carbon, K, was estimated as described elsewhere (Nielsen, J., J. Villadsen, and G. Liden. 2003. Bioreaction engineering principles, p.60-73. Kluwer Academic/Plenum Publishers, New York).
$^c$Degree of reduction balance ($\Delta\kappa$) is estimated as:

$$\sum_{over\ i\ reactants} v_i c_i \kappa_i - \sum_{over\ j\ products} v_j c_j \kappa_j$$

where v and c are the stoichiometric coefficients and the number of carbon atoms for each compound, respectively.
$^d$Net redox units, H, are expressed per mole of glycerol (H ≡ NAD(P)H ≡ FADH$_2$ ≡ "H$_2$").
$^e$Cell mass formula is the average of reported for different microorganisms, including bacteria, yeast, and fungi (Nielsen et al., 2003). Conversion of glycerol into cell mass neglects carbon losses as 1-C metabolites. In consequence, the degree of reduction balance in this case represents the minimum amount of redox units generated.
$^f$Similar results are obtained by considering the conversion of glycerol to ethanol and glycerol to H$_2$—CO$_2$.

TABLE 2

Analysis of redox balance for the conversion of glycerol into cell mass and selected fermentation products.

| Pathway | Stoichiometry$^a$ ($\kappa^b$) | $\Delta\kappa^c$ (H$^d$) |
|---|---|---|
| glycerol → cell mass | $C_3H_8O_3$ (14/3) → $3CH_{1.9}O_{0.5}N_{0.2}$(4.3)$^e$ | 1.1 (0.55H) |
| glycerol → 1,2-PDO | $C_3H_8O_3$ (14/3) → $C_3H_8O_2$ (16/3) | −2 (−1H) |
| glycerol →1,3-PDO | $C_3H_8O_3$ (14/3) → $C_3H_8O_2$ (16/3) | −2 (−1H) |

$^{a-f}$as above.

TABLE 3

Analysis off redox balance for the conversion of sugars into cell mass and selected fermentation products. The synthesis of cell mass results in the net consumption of reducing equivalents (i.e., $\Delta\kappa$ < 0). Products are synthesized through pathways that result in either net consumption of reducing equivalents (i.e., $\Delta\kappa$ < 0) or neutral pathways (i.e., $\Delta\kappa$ = 0). Redox balance in such cases can be achieved in the absence of electron acceptors.

| Pathway | Stoichiometry$^a$ ($\kappa^b$) | $\Delta\kappa^c$ (H$^d$) |
|---|---|---|
| glucose → cell mass | $C_6H_{12}O_6$(4) → $6CH_{1.9}O_{0.5}N_{0.2}$(4.3)$^e$ | −1.8 (−0.9H) |
| glucose → ethanol + formate$^f$ | $C_6H_{12}O_6$(4) → $2C_2H_6O$(6) + $2CH_2O_2$(2) | −4 (−4H) |
| glucose → ethanol + CO$_2$$^f$ | $C_6H_{12}O_6$(4) → $2C_2H_6O$(6) + $2CO_2$(0) | 0 (0H) |
| glucose → succinate | $C_6H_{12}O_6$(4) + $2CO_2$(0) → $2C_4H_6O_4$(14/4) | −4 (−2H) |
| glucose → propionate | $C_6H_{12}O_6$(4) → $2C_3H_6O_2$(14/3) | −4 (−2H) |
| glucose → lactate | $C_6H_{12}O_6$(4) → $2C_3H_6O_3$(12/3) | 0 (1H) |
| glucose → alanine | $C_6H_{12}O_6$(4) → $2C_3H_7NO_2$(12/3) | 0 (1H) |

$^{a-e}$as above.
$^f$Two alternative pathways are presented for the conversion of glucose to ethanol, which differ in the co-product synthesized along with ethanol (carbon dioxide or formate) and the overall redox balance (redox consuming or redox neutral).

The present techniques address disadvantages associated with anaerobic fermentation of reduced carbon sources such as glycerol and the by-products created during the production of chemical products from glycerol. Under anaerobic conditions, the conversion of glycerol into cell mass results in the net gain of reducing equivalents (Table 1). The conversion of glycerol into succinate or lactate, for example, does not consume the excess reducing equivalents generated by the conversion of glycerol into cell mass; in the case of converting glycerol into lactate, the redox balance is further perturbed by a net gain of two reducing equivalents. This redox potential imbalance can be ameliorated through the co-production of a chemical like 1,3 -propanediol (1,3-PDO) from glycerol, which results in the net consumption of two reducing equivalents. However, while the conversion of glycerol into 1,3-PDO enables cell growth by facilitating redox-balanced conditions, it also creates an undesirable by-product that may interfere with the efficient separation of the desired target chemical from the product mixture. The techniques provided herein, through the use of limiting amounts of electron acceptors to consume excess reducing equivalents generated by the incorporation of glycerol into cell mass, reduce or eliminate the production of undesirable by-products and allow increased yield of product.

Figure 3:
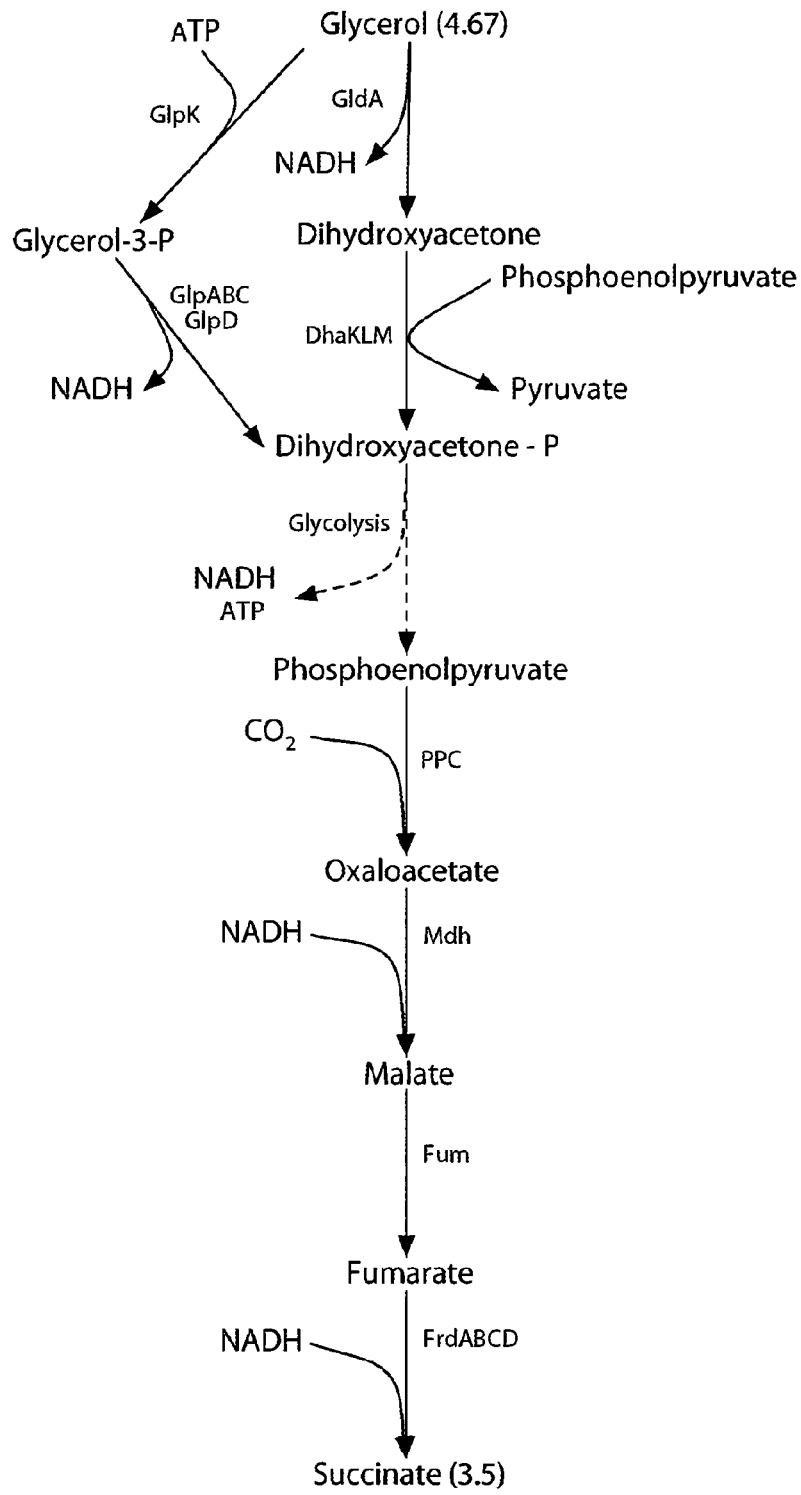
FIG. 3 illustrates the pathway for producing succinate from glycerol in accordance with the present techniques.
Figure 4:
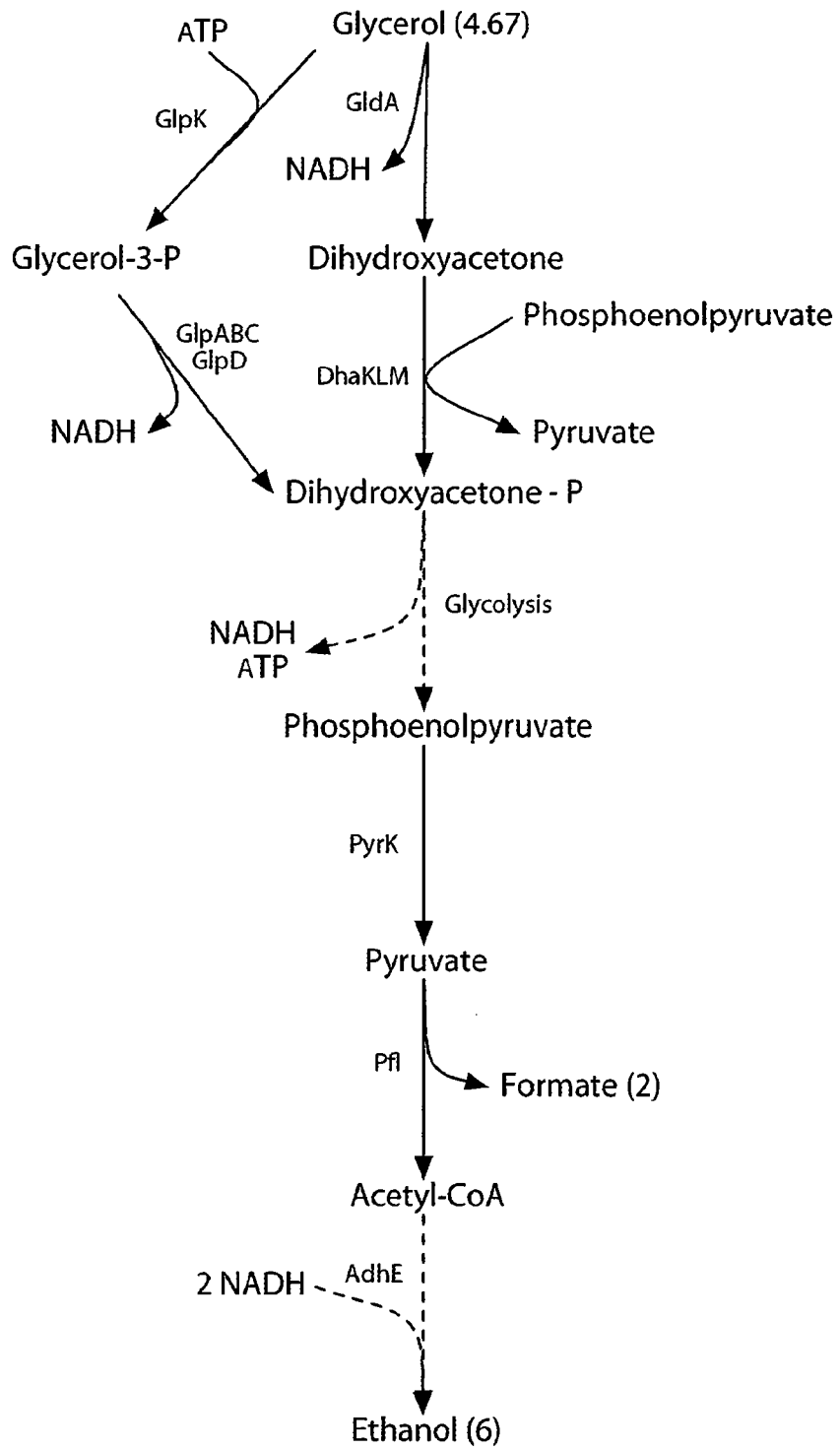
FIG. 4 illustrates the pathway for producing ethanol from glycerol in accordance with the present techniques.
Figure 5:
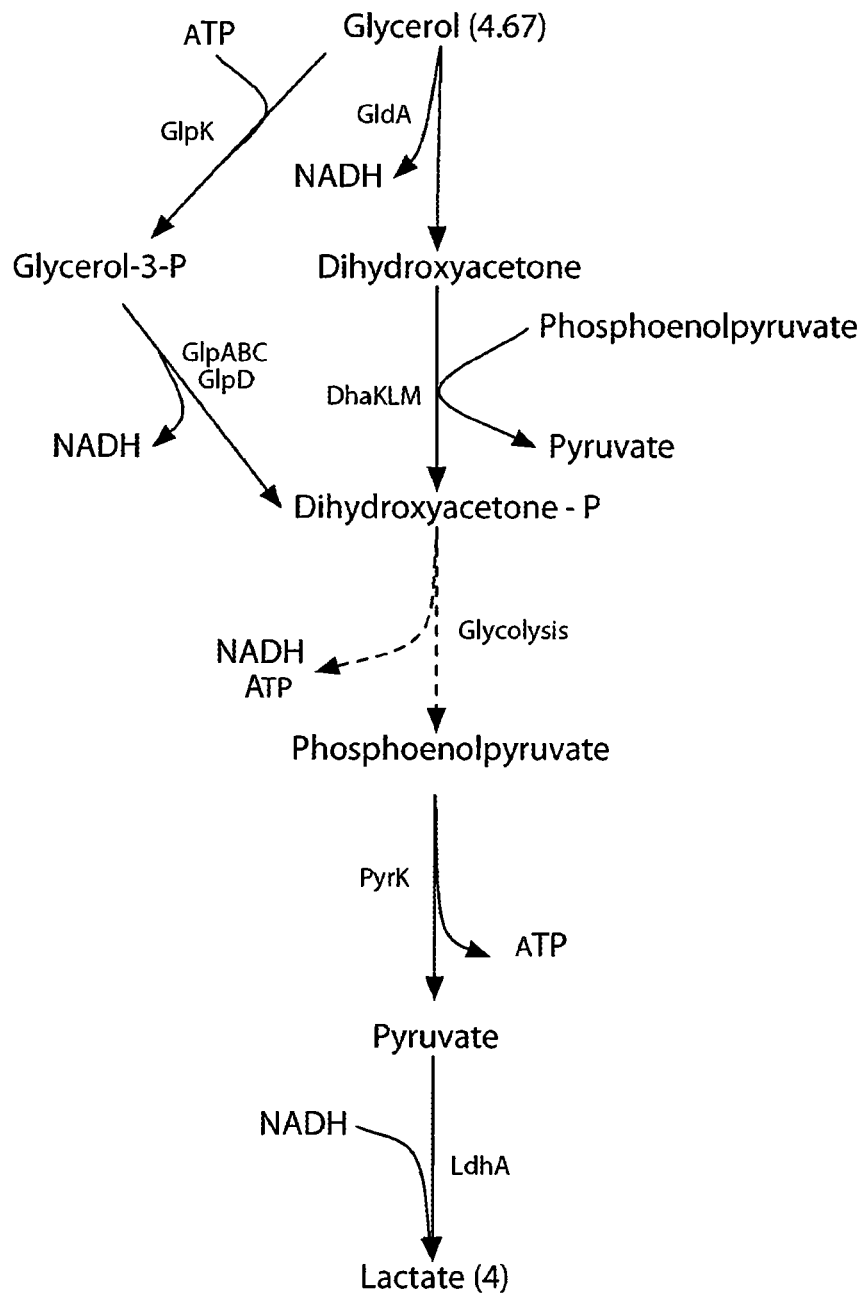
FIG. 5 illustrates the pathway for producing lactate from glycerol in accordance with the present techniques.

The proposed strategy is illustrated in FIGS. 3, 4, and 5 which schematically depict the production of succinate; or ethanol and formic acid (which is converted to ethanol and H$_2$); or lactate from glycerol. The advantage of using glycerol is evident when the synthesis of a product from other sugars, such as glucose, is considered, because the use of glucose, xylose or similar sugars results in a shortage of reducing equivalents that clearly limits the theoretical yield. Consequently, the maximum theoretical yield of succinate from glycerol is at least 15% higher than that from sugars such as glucose. In addition, synthesis of ethanol from sugars results in a maximum theoretical yield of approximately 51% w/w, regardless of whether glucose or xylose is used as carbon source. Accordingly, the use of glycerol as a carbon source provides increased yield of products such as succinate and ethanol. However, in certain embodiments, it may be useful to use other reduced carbon sources as feedstocks for the reaction.

Figure 6A:
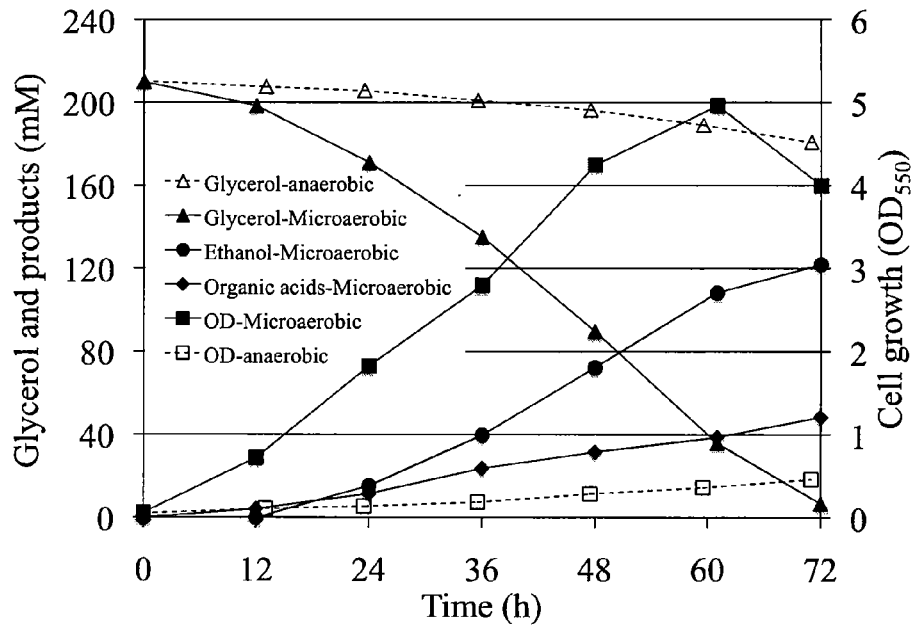
FIG. 6A is a graph comparing the fermentation of glycerol in a wild-type bacterial strain under microaerobic conditions and anaerobic conditions.
Figure 6B:
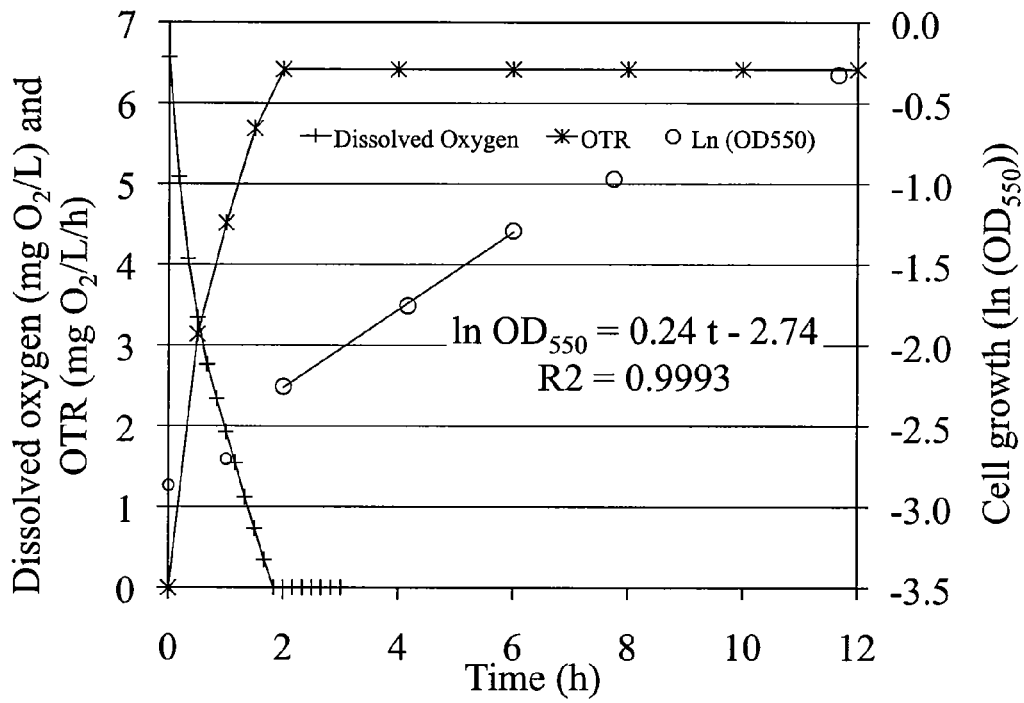
FIG. 6B is a graph showing a characteristic profile of dissolved oxygen, OTR (volumetric oxygen transfer rate) and cell growth ($OD_{550}$) in a wild-type bacterial strain under microaerobic conditions.
Figure 7:
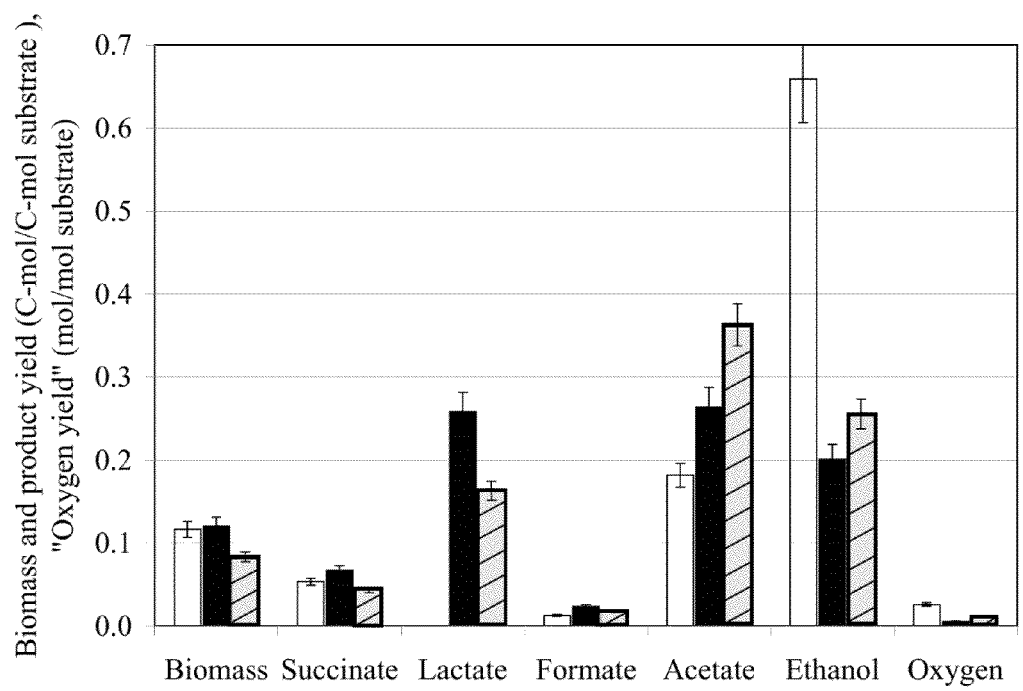
FIG. 7 is a bar graph comparing the product and biomass yields of the fermentation of glycerol (solid bars), glucose (clear bars) and xylose (hatched bars) in a wild-type bacterial strain under microaerobic conditions. Data is also shown for "oxygen yield", which represents the amount of oxygen consumed in the metabolism of the specific substrate.

As shown in FIG. 6, FIG. 7, FIG. 8, and FIG. 9 glycerol may be used to produce ethanol, lactic acid, and succinic acid by wild-type *E. coli*. Glycerol utilization by wild-type *E. coli* strain MG1655 under microaerobic conditions led to the synthesis of reduced compounds ethanol and succinate as the major products, although the amount of acetate was increased (FIG. 6 and FIG. 7). Moreover, much larger concentrations of succinate were produced under microaerobic conditions (FIG. 6) with improved product yields (FIG. 7) as compared to the succinate production under anaerobic conditions. In terms of productivity, 10 g/L of glycerol were completely consumed by the MG1655 wild-type strain under microaerobic conditions in about 60 hours, which corresponds to approximately 2-fold increase in productivity of the microaerobic production of succinate vs. anaerobic production of succinate.

Figure 8A:
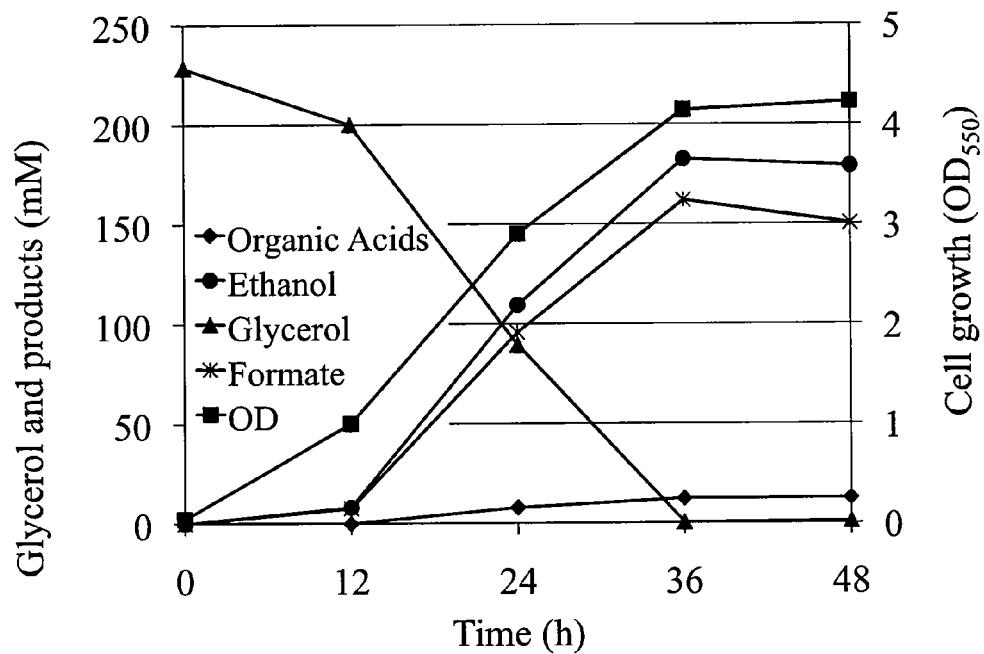
FIG. 8A is a graph comparing the production of ethanol, formate, and organic acids from glycerol under microaerobic conditions in a strain SY04 [pZSKLMg1dA], which was engineered for the co-production of ethanol and formate (i.e. $\Delta$pta, $\Delta$frdA, $\Delta$fdhF, gldA+, dhaKLM+)
Figure 8B:
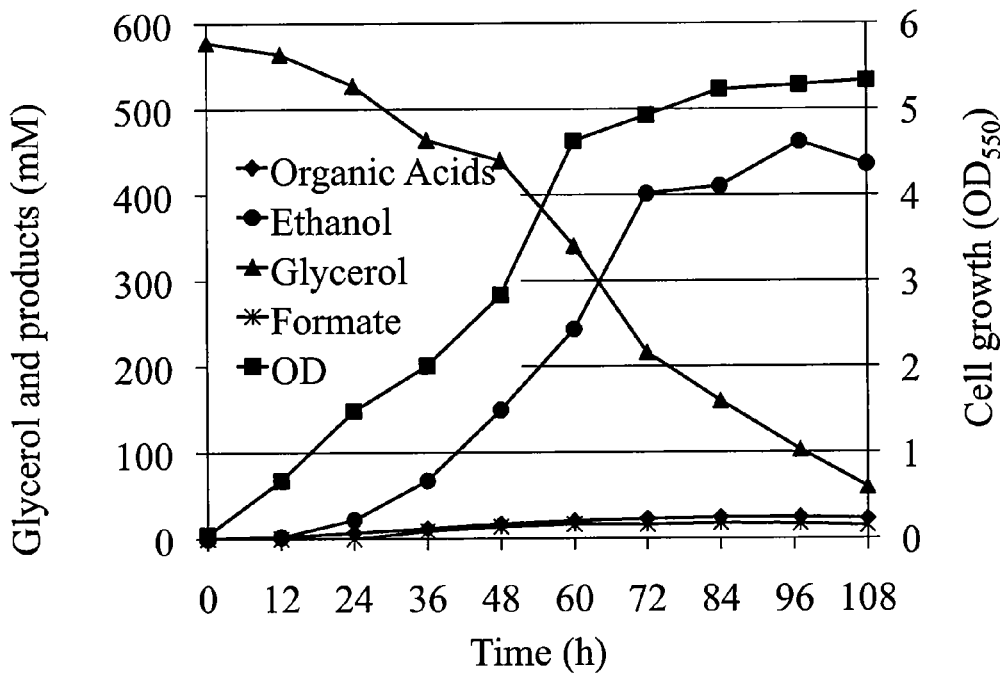
FIG. 8B is a graph comparing the production of ethanol, formate, and succinate from glycerol under microaerobic conditions in a mutagenic strain EH05 (pZSKLMg1dA), which was engineered for the co-production of ethanol and hydrogen (i.e. $\Delta$pta, $\Delta$frdA, $\Delta$ldhA, gldA+, dhaKLM+)

In addition, mutant bacterial strains were evaluated for their ability to produce products whose synthesis results in no net generation or consumption of reducing equivalents. Degree of reduction analysis of the pathways involved in the conversion of glycerol to these products yields a degree of reduction balance of $\Delta\kappa=0$. For example, production of ethanol (along with co-products formate or hydrogen) is one of the products in this category. Evaluation of recombinant strain SY03 (pZSKLMgldA=$\Delta$pta, $\Delta$frdA, +gldA, +dhaKLM), a derivative of *E. coli* strain MG1655 containing mutations that reduce the synthesis of acetate ($\Delta$pta), and succinate ($\Delta$frdA) and overexpression of the enzymes glycerol dehydrogenase (gldA) and dihydroxyacetone kinase (dhaKLM), showed that ethanol was produced as the main fermentation product at yields close to the maximum theoretical (FIG. 8A). The ethanol yield was 0.96 mole/mole of glycerol utilized and volumetric productivities for glycerol utilization and ethanol synthesis were 4.65 mole/L/h and 4.61 mole/L/h, respectively (FIG. 8B). The high productivities realized were the result of both higher cell density and higher specific rates under microaerobic conditions, compared to those obtained with the use of anaerobic conditions. The microaerobic conditions used were characterized by a volumetric oxygen transfer rate of 5 mg $O_2$/L/h.

Figure 9A:
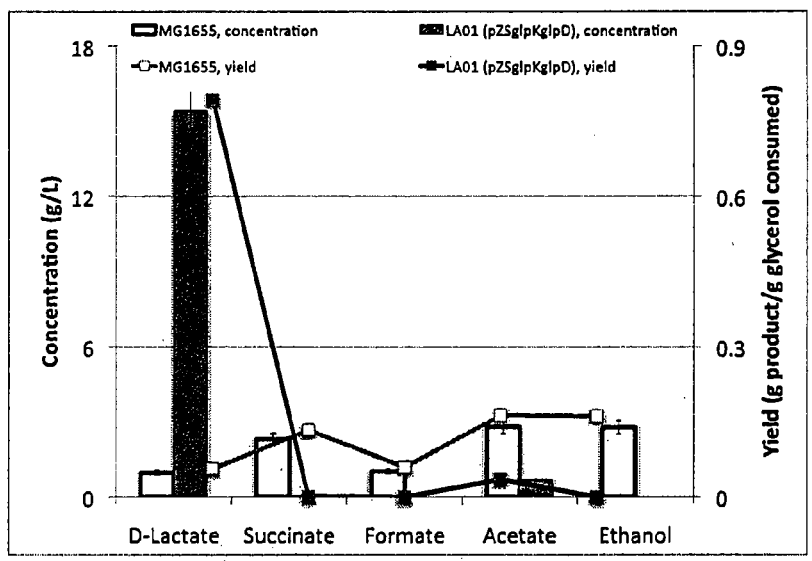
FIG. 9A is a bar graph comparing the product yields of the fermentation of glycerol in wild-type MG1655 and strain LA01 (pZSglpKglpD) engineered for the production of D-lactate under microaerobic conditions (i.e. $\Delta$pflB, $\Delta$frdA, glpK+, glpD+)
Figure 9B:
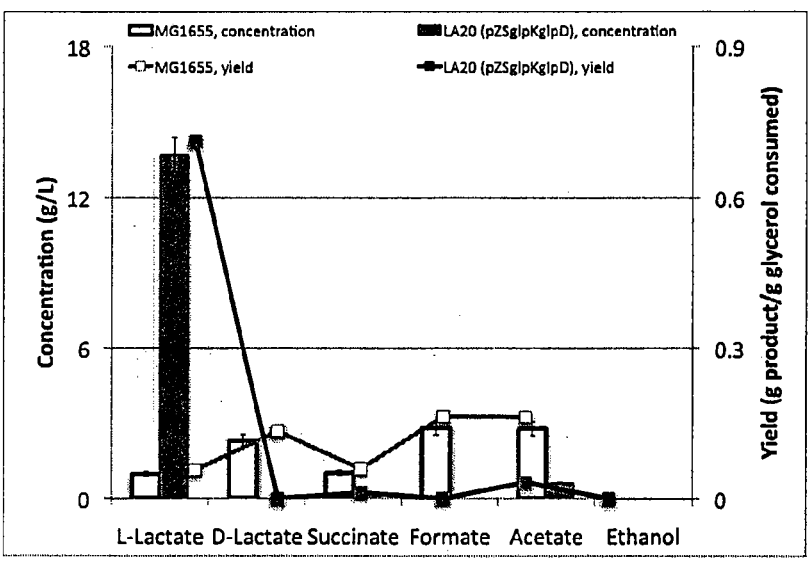
FIG. 9B is a bar graph comparing the concentration of products of the fermentation of glycerol in wild-type MG1655 and strain LA20 (pZSglpKglpD) engineered for the production of L-lactate under microaerobic conditions (i.e. $\Delta$frdA $\Delta$pta $\Delta$adhE $\Delta$mgsA $\Delta$ldhA(ldhbovis), glpK+, glpD+)
Figure 9C:
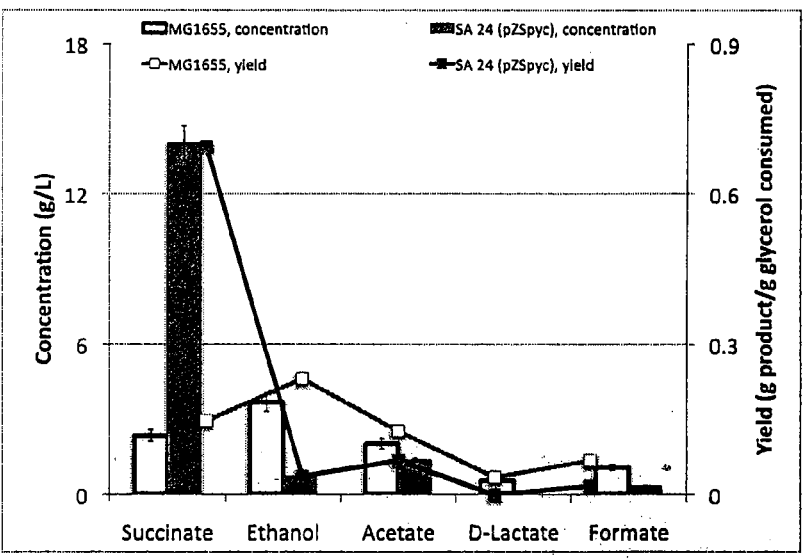
FIG. 9C is a bar graph comparing the concentration of products of the fermentation of glycerol in wild-type MG1655 and strain SA24 (pZSpyc) engineered for the production of succinate under microaerobic conditions (i.e. $\Delta$adhE $\Delta$pta $\Delta$poxB $\Delta$ppc, pyc+)

Another group of products that may be generated under microaerobic conditions according to the present techniques are those whose synthesis from glycerol or other reduced carbon sources results in the net generation of reducing equivalents ($\Delta\kappa>0$), such as lactate. The feasibility of this approach is illustrated in FIGS. 9A, 9B, and 9C, which show increased production of lactic acid and succinic acid by a combination of appropriate microaerobic conditions and specific genetic manipulations. The microaerobic conditions used in these experiments were characterized by a volumetric oxygen transfer rate of 20 mg $O_2$/L/h.

EXAMPLE 1

Microorganisms

It is envisioned that any appropriate microbial strain may be used with the present techniques, including members of the genera *Aspergillus, Saccharomyces, Zygosaccharomyces, Pichia, Kluyveromyces, Candida, Hansenula, Dunaliella, Debaryomyces, Mucor, Torylopsis, Bacillus, Paenibacillus* and *Escherichia*. A suitable microbial strain for the microbial synthesis process may be any wild type strain capable of producing the reduced chemical compound of interest. In addition, a suitable microbial strain may be obtained and/or improved by subjecting a parent strain of interest to a classical mutagenic treatment or to recombinant DNA techniques. Furthermore, such strains may then be subjected to sequential selection processes of metabolic evolution in which progeny strains are evaluated for improved performance under the desired reaction conditions. For example, such strains may be selected on the basis of high-performing biocatalysts. Markers of improved performance of a progeny strain may be increased production or yield of the desired chemical product from the glycerol feedstock. In one embodiment, metabolic evolution is conducted in the presence of decreasing amounts of oxygen, nitrate, nitrite or other electron acceptor.

Genes that will positively affect the production of the desired chemical product may be expressed in suitable hosts. For example it may be highly desirable to over-express certain enzymes in the glycerol to dihydroxyacetone pathway and/or other pathways at levels far higher than currently found in wild type cells. As shown in FIGS. 8A and B, and FIGS. 9A, 9B, and 9C the overexpression of gldA in a suitable microbial host in combination with the inhibition of enzymes involved in competing pathways may increase the production of succinate, ethanol, or lactic acid.

Recombinant organisms that have been genetically engineered to express one or more exogenous polynucleotide coding sequences, i.e., a gene sequence that is not native, or endogenous, to the host organism can also be used in the invention. Overexpression of desired genes may be accomplished by the selective cloning of the genes encoding those enzymes into multicopy plasmids or placing those genes under a strong inducible or constitutive promoter. Methods for overexpressing desired proteins are common and well known in the art of molecular biology. It is envisioned that any of the genes provided in Table 4 may be overexpressed in a microbial strain.

TABLE 4

Genes Involved in the Production of Reduced Chemical Compounds

| Protein | Gene | GenBank Acc. No. |
|---|---|---|
| glycerol dehydrogenase | gldA | ECK3937 |
| dihydroxyacetone kinase subunit K | dhaK | ECK1186 |
| dihydroxyacetone kinase subunit L | dhaL | ECK1187 |
| dihydroxyacetone kinase subunit M | dhaM | ECK1188 |

TABLE 4-continued

Genes Involved in the Production of Reduced Chemical Compounds

| Protein | Gene | GenBank Acc. No. |
|---|---|---|
| glycerol kinase | glpK | ECK3918 |
| glycerol-3-P dehydrogenase subunit A | glpA | ECK2233 |
| glycerol-3-P dehydrogenase subunit B | glpB | ECK2234 |
| glycerol-3-P dehydrogenase subunit C | glpC | ECK2235 |
| glycerol-3-P dehydrogenase subunit D | glpD | ECK3412 |
| phosphoenolpyruvate carboxykinase | pckA | ECK3390 |
| phosphoenolpyruvate carboxylase | ppc | ECK3947 |
| formate hydrogen lyase | fdhF | ECK4072 |
| formate hydrogen lyase subunit | hycC | ECK2718 |
| formate hydrogen lyase subunit | hycD | ECK2717 |
| lactate dehydrogenase | ldhA | ECK1377 |
| alcohol dehydrogenase | adhE | ECK1235 |
| alcohol dehydrogenase mutant (mutant active in the presence of electron acceptors) | adhE* | ECK1235 |
| glycerol dehydratase (capable of converting glycerol into hydroxyacetone or 3-hydroxypropionaldehyde) | dhaB (from *Klebsiella pneumoniae*) | EF634063 |
| phosphoenolpyruvate carboxykinase | pckA (from *Actinobacillus succinogenes*) | Asuc_0221 |
| dihydroxyacetone kinase subunit KL | dhaKL (from *Citrobacter freundii*) | DQ473522 |
| pyruvate carboxylase | pyc (from *Lactobacillus lactis*) | AF068759 |
| pyruvate carboxylase | pyc (from *Rhizobium etli*) | U51439 |
| pyruvate decarboxylase | pdc (*Zymomonas mobilis*) | |
| phosphoenolpyruvate carboxykinase | pckA (*E. coli*) | |
| malic enzyme | maeA and maeB (*E. coli*) | |
| methylmalonyl-CoA mutase | scpA (*E. coli*) | |
| methylmalonyl-CoA decarboxylase | scpB (*E. coli*) | |
| propionyl-CoA: succinate CoA transferase | scpC (*E. coli*) | |
| GTPase that interacts with methylmalonyl-CoA mutase | argK (*E. coli*) | |
| subunit of E1p component of pyruvate dehydrogenase complex | aceE (*E. coli*) | |
| lipoate acetyltransferase/dihydrolipoamide acetyltransferase, subunit of pyruvate dehydrogenase multienzyme complex | aceF (*E. coli*) | |
| E3 monomer, subunit of pyruvate dehydrogenase multienzyme complex | lpdA (*E. coli*) | |
| Fumarate reductase | frdABCD (*E. coli*) | |
| phosphoenolpyruvate carboxylase | ppc (*E. coli*) | |

In addition to the cells exemplified it is contemplated that the present method will be able to make use of cells having single or multiple mutations specifically designed to enhance the production of the desired end product. Cells that normally divert a carbon feed stock into non-productive pathways, or that exhibit significant catabolite repression could be mutated to avoid these phenotypic deficiencies. For example, many wild type cells are subject to catabolite repression from glucose and by-products in the media and it is contemplated that mutant strains of these wild type organisms would be particularly useful in certain embodiments of the present techniques. In particular, it is envisioned that any of the genes in Table 5 may be mutated, either alone or in combination with other genes, in a microbial organism for use in the present techniques. As defined herein, microorganisms that lack an indicated gene are considered to be knock outs of that gene.

TABLE 5

Genes Involved in By-Product Pathways

| Protein | Gene | GenBank Acc. No. |
|---|---|---|
| fumarate reductase (subunits A-D) | frd | ECK4147-ECK4150 |
| lactate dehydrogenase | ldhA | ECK1377 |
| D-lactate dehydrogenase, membrane-bound | dld | ECK2126 |
| L-lactate dehydrogenase, membrane-bound | lldD | ECK3595 |
| methylglyoxal synthase | mgsA | ECK0954 |
| glyoxalase I | gloA | ECK1647 |
| glyoxalase II | gloB, gloC | ECK0212 |
| acetaldehyde dehydrogenase subunit | aldA | ECK1408 |
| acetaldehyde dehydrogenase subunit | aldB | ECK3577 |
| phosphate acetyltransferase | pta | ECK2291 |
| acetate kinase | ackA | ECK2290 |
| alcohol dehydrogenase | adhE | ECK1235 |
| ethanol dehydrogenase | adhP | ECK1472 |
| pyruvate formate-lyase | pflB | ECK0894 |
| pyruvate oxidase | poxB | ECK0862 |
| pyruvate dehydrogenase | aceE, aceF, lpdA | ECK0113-ECK0115 |
| nitrite reductase nrf operon | nrf ABCDEFG | ECK4063-ECK4069 |
| nitrite reductase nap operon | nap CBHGADF | ECK2194-ECK2200 |
| nitrite/nitrate transporter subunits ABD | nir | ECK3353-ECK3355 |
| nitrate/nitrite regulatory protein | nar LXKGHJI | ECK1215-ECK1221 |
| Formate dehydrogenase | fdnG | ECK1468 |
| Formate dehydrogenase | fdoG | ECK3887 |
| Formate dehydrogenase | fdhF | ECK4072 |
| triose phosphate isomerase | tpiA | ECK3911 |
| fumarate reductase | fumA, fumB, fumC | ECK1607 |
| fumarate reductase | fumA, fumB, fumC | ECK4115 |
| fumarate reductase | fumA, fumB, fumC | ECK1606 |
| F0F1-ATPase | atpF, atpD | ECK3729 |

TABLE 5-continued

Genes Involved in By-Product Pathways

| Protein | Gene | GenBank Acc. No. |
|---|---|---|
| F0F1-ATPase | atpF, atpD | ECK3725 |
| phosphoenolpyruvate synthase | pps | ECK1700 |
| phosphoenolpyruvate carboxykinase | pckA | ECK3390 |
| phosphoenolpyruvate carboxylase | ppc | ECK3947 |
| Malate dehydrogenase | mdh | ECK3225 |

Figure 10:
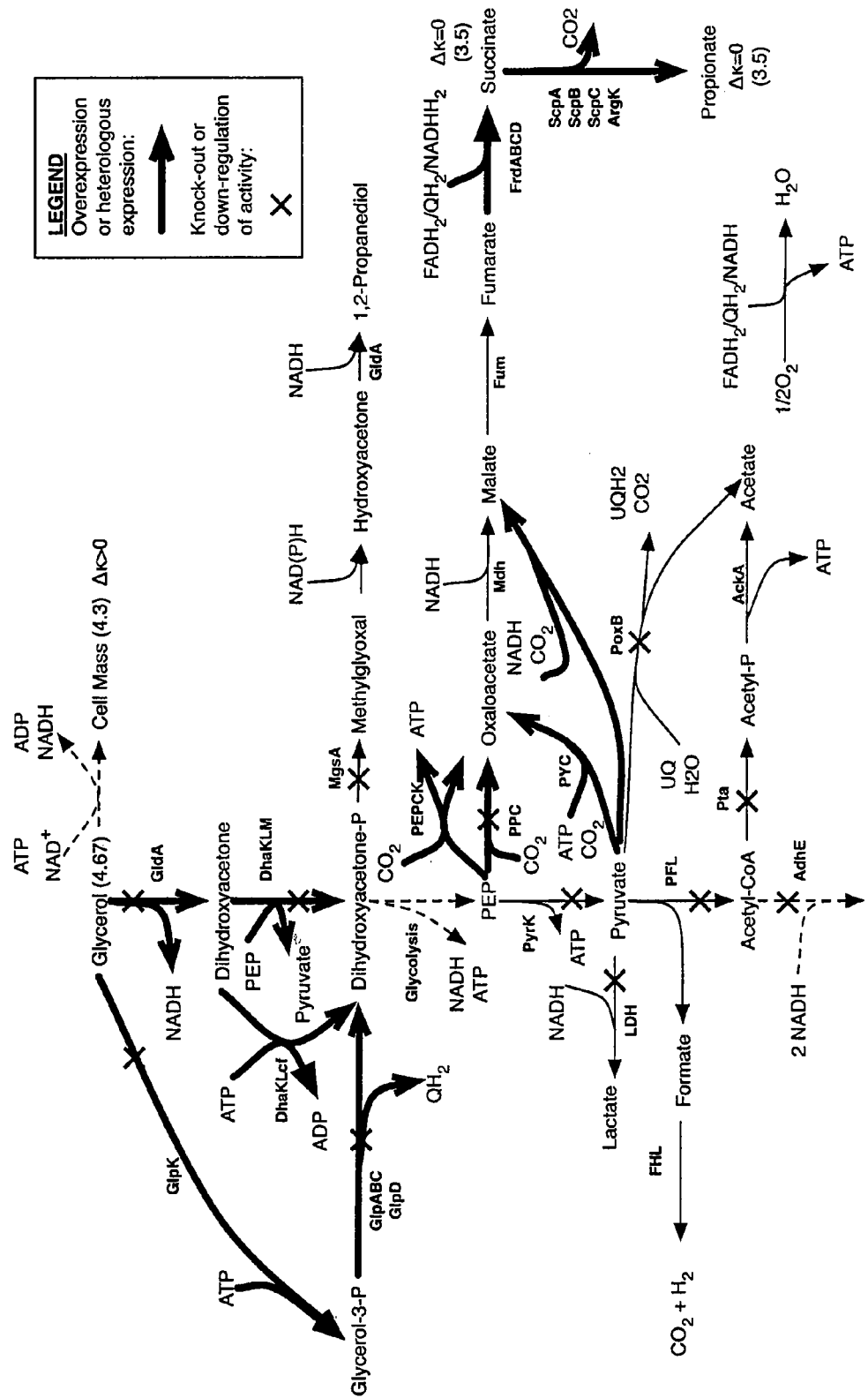
FIG. 10 illustrates the pathways engineered for the production of succinate from glycerol in exemplary mutagenic microorganisms in accordance with the present techniques.

For example, as noted above, FIG. 10 depicts a schematic pathway for the production of succinate or propionate from glycerol in accordance with the present techniques. In such an embodiment, it may be advantageous to provide an organism in which the one or more genes involved in the pathway to convert acetyl-CoA to ethanol are mutated or inhibited in some way such that their catalytic activity is reduced. In a specific embodiment, a suitable microorganism may include a mutation of the adhE gene. Additional mutations may involve the mutation of the pta, ackA, or poxB genes involved in acetate formation; the ppc gene involved in the conversion of phosphoenolpyruvate into oxaloacetate; the glpABC operon, glpD, or glpK, involved in the conversion of glycerol to glycerol-3-P to dihydroxyacetone phosphate; or dhaKLM involved in the conversion of dihydroxyacetone to dihydroxyacetone phosphate. These mutations or combinations thereof may be combined with the overexpression of either endogenous or heterologous genes, including but not limited to: gldA from *E. coli* and comparable genes from other organisms; dhaKLcf from *Citrobacter freundii*; pepck from *Actinobacillus succinogenes*; or pyc from *Rhizobium etli*.

Figure 11:
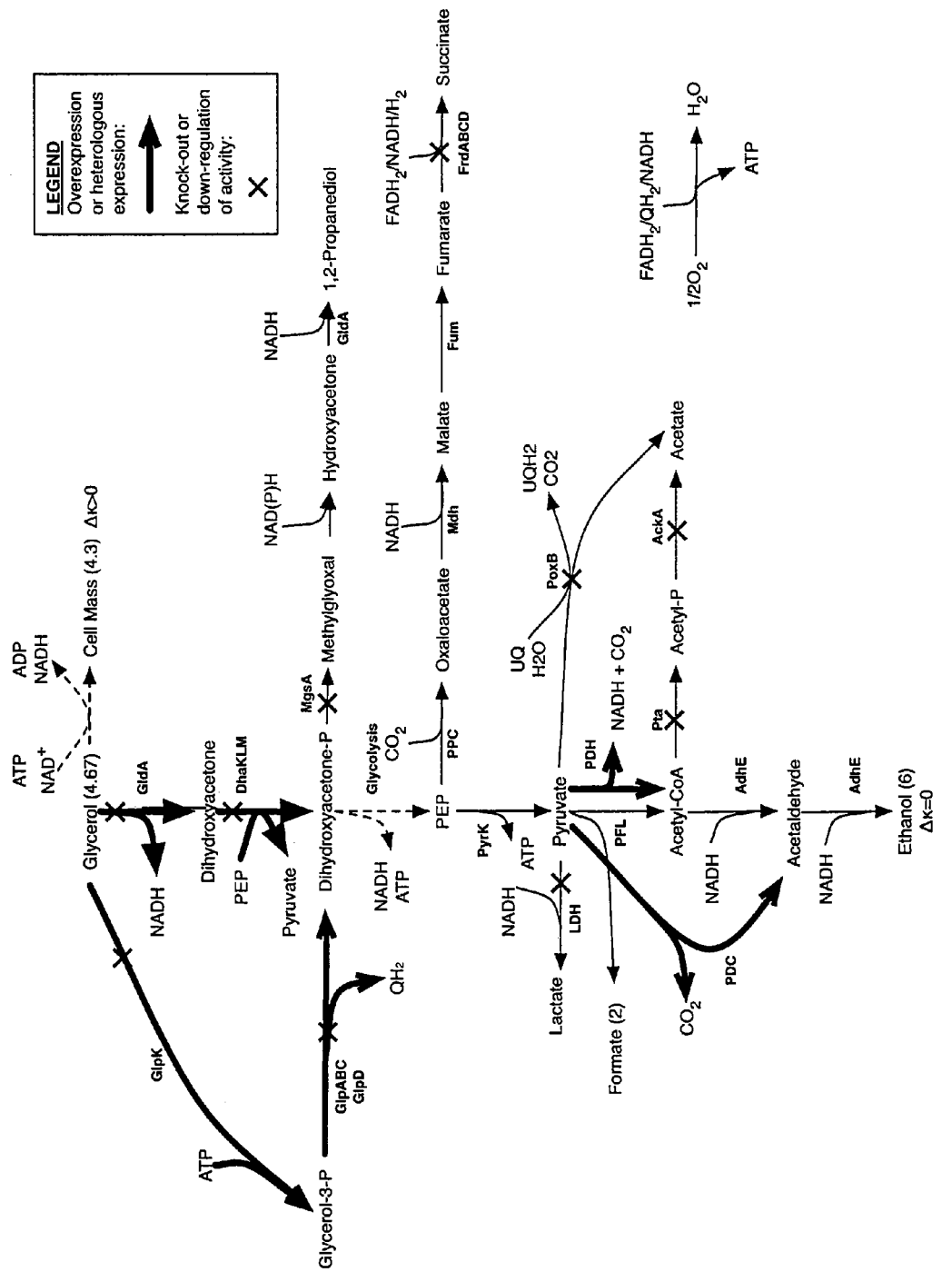
FIG. 11 illustrates the pathways engineered for the production of ethanol from glycerol in exemplary mutagenic microorganisms in accordance with the present techniques.

In another embodiment, shown in FIG. 11, ethanol production from glycerol may be increased through the inhibition of competing pathways that produce acetate and succinate byproducts. These mutations may involve the mutation of the pta, ackA, or poxB genes involved in acetate formation; the frdABCD operon involved in succinate formation; the glpABC operon, glpD or glpK, involved in the conversion of glycerol to dihydroxyacetone phosphate. These mutations or combinations thereof may be combined with the overexpression of either endogenous or heterologous genes, including but not limited to: gldA from *E. coli* and comparable genes from other organisms or dhaKLcf from *Citrobacter freundii*.

Figure 12:
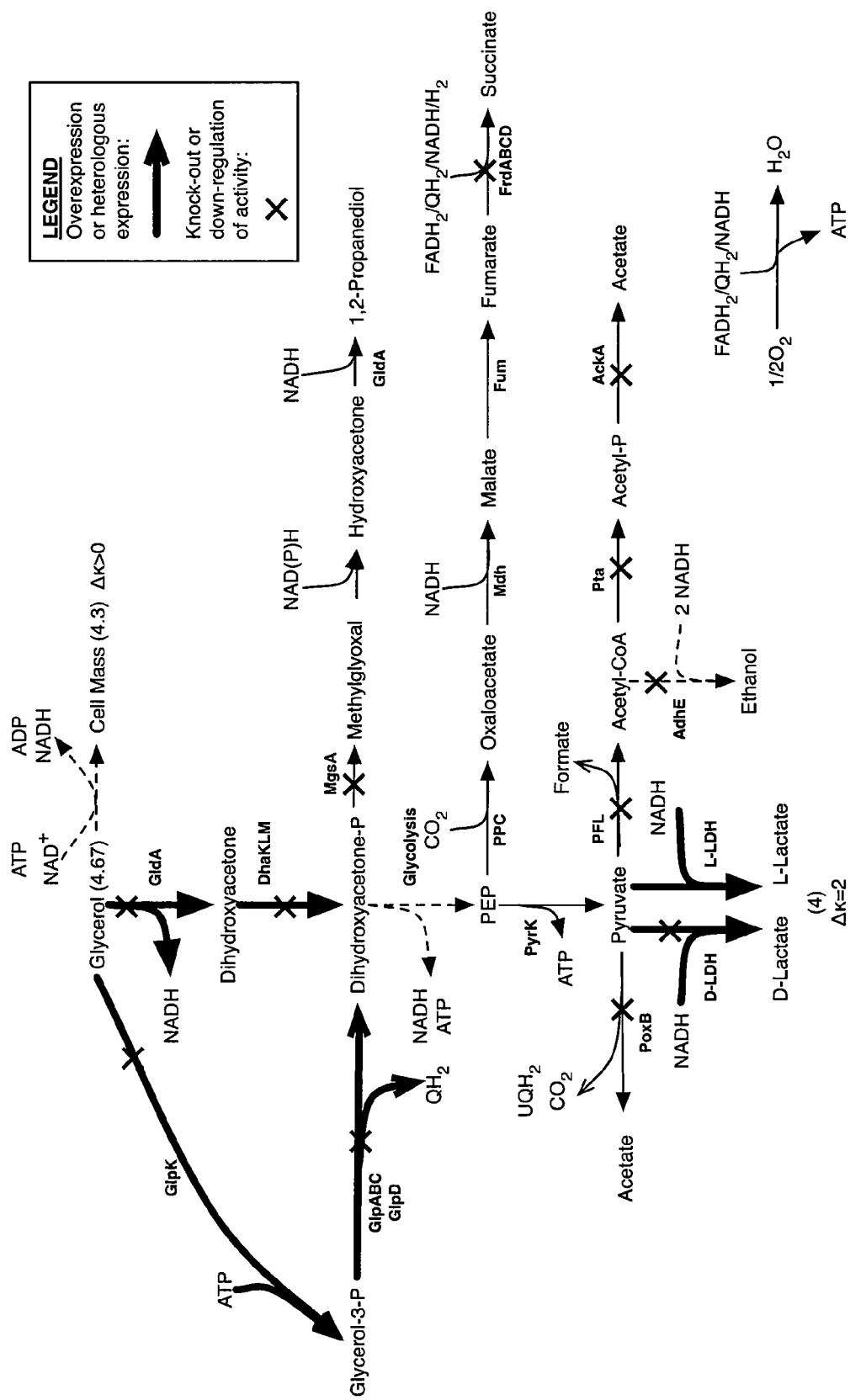
FIG. 12 illustrates the pathway engineered for the production of lactate from glycerol in exemplary mutagenic microorganisms in accordance with the present techniques.

In an additional embodiment, shown in FIG. 12, lactate production from glycerol may be increased through the inhibition of competing pathways that produce acetate, succinate, and ethanol by-products. These mutations may involve the mutation of the pta, ackA, or poxB genes involved in acetate formation; the frdABCD operon involved in succinate formation; the adhE gene involved in ethanol formation. Further genetic alterations may involve overexpression of the glpABC operon, glpD or glpK, involved in the conversion of glycerol to dihydroxyacetone phosphate.

Methods of creating mutants are common and well known in the art. For example, wild type cells may be exposed to a variety of agents such as radiation or chemical mutagens and then screened for the desired phenotype. Specific methods for creating mutants using radiation or chemical agents are well documented in the art. After mutagenesis has occurred, mutants having the desired phenotype may be selected by a variety of methods. Random screening is most common where the mutagenized cells are selected for the ability to produce the desired product. Alternatively, selective isolation of mutants can be performed by growing a mutagenized population on selective media where only resistant colonies can develop. In one embodiment, cells may be subjected to mutagenesis prior to or during selection for metabolic evolution. Targeted mutagenesis through recombinant techniques can also be employed separately, or in combination with random mutagenic techniques.

EXAMPLE 2

Media and Growth Conditions

Typically cells are grown at 37° C. in appropriate media, although some bacteria have temperature optima at 35, 37, 39, or 41° C. Preferred growth media according to the present techniques may include minimal media or minimal salt media. For example, suitable media may include 4-morpholinepropanesulfonic acid media (MOPS). In certain embodiments, the phosphate salts in the media may be replaced with sodium salts. Glycerol feedstock may be provided in any suitable amount. For example, glycerol may be provided at 10 g/L.

Suitable pH ranges for the fermentation may be between pH 5.0 to pH 9.0. It is envisioned that alkaline pH may be suitable for improved yield of certain products while acidic pH may be suitable for improved yield of other products. For example, acidic pH may promote production of ethanol and hydrogen while alkaline pH may promote the production of ethanol and formic acid.

Fermentations may be conducted in any suitable microaerobic or microrespiratory fermentation system. It is envisioned that room air, oxygen, and/or nitrogen may be provided to the system in suitable amounts and at a suitable rate such that, as the growth rate of the microbes approaches log phase, there are substantially no detectable electron acceptors in the culture.

The present process may employ a batch method of fermentation. As used herein, "fermentation" may refer to microbial growth under microaerobic or microrespiratory conditions suitable for the production of reduced chemical products from glycerol. A classical batch fermentation may be a closed system where the composition of the media is set at the beginning of the fermentation and not subject to artificial alterations during the fermentation. Thus, at the beginning of the fermentation the media is inoculated with the desired organism or organisms and fermentation is permitted to occur adding nothing to the system. Typically, however, a "batch" fermentation is batch with respect to the addition of carbon source and attempts are often made at controlling factors such as pH and oxygen concentration. In batch systems the metabolite and biomass compositions of the system change constantly up to the time the fermentation is stopped. Within batch cultures cells progress through a static lag phase to a high growth log phase and finally to a stationary phase where growth rate is diminished or halted.

Sequential fermentation processes are also suitable in the present invention and comprise a typical batch system with the exception that the substrate is added in increments as the fermentation progresses. A fed-batch strategy, for example, may be advantageous. A fed-batch fermentation is an open system where a defined fermentation medium is added at the beginning of the fermentation and is inoculated with the desired organism or organisms and the fermentation is permitted to occur. In addition to the adjustments typically made in a batch fermentation, to pH or oxygen concentration, for example, a fed-batch fermentation involves the periodic or continuous addition of the carbon source and any additional limiting nutrients, with little or no removal of culture medium from the fermentation reaction during the fermentation process.

It is contemplated that the present techniques would also be adaptable to continuous fermentation methods. Continuous fermentation is an open system where a defined fermentation media is added continuously to a bioreactor and an equal amount of conditioned media is removed simultaneously for processing. Continuous fermentation generally maintains the cultures at a constant high density where cells are primarily in log phase growth. Continuous fermentation allows for the modulation of one factor or any number of factors that affect cell growth or end product concentration. It is contemplated that the present invention may be practiced using either batch, fed-batch or continuous processes and that any known mode of fermentation would be suitable. Additionally, it is contemplated that cells may be immobilized on a substrate as whole cell catalysts and subjected to fermentation conditions for production of reduced products from glycerol.

While the invention may be susceptible to various modifications and alternative forms, specific embodiments have been shown by way of example in the drawings and have been described in detail herein. However, it should be understood that the invention is not intended to be limited to the particular forms disclosed. Rather, the invention is to cover all modifications, equivalents, and alternatives falling within the spirit and scope of the invention as defined by the following appended claims.

What is claimed is:

1. An *Escherichia coli* strain comprising:
   a disruption in one or more of a adhE gene (encoding alcohol dehydrogenase), a pta gene (encoding phosphate acetyltransferase), a poxB gene (encoding pyruvate oxidase), a ppc gene (encoding phospoenolpyruvate carboxylase) or a dhaK gene (encoding dihydroxyacetone kinase subunit K);
   an exogenous *Citrobacter freundii* dhaKL gene (encoding dihydroxyacetone kinase subunits KL); and
   an exogenous *Actinobacillus succinogenes* pckA gene (encoding phosphoenolpyruvate carboxykinase).

2. An *Escherichia coli* strain comprising:
   an overexpressed gldA gene (encoding glycerol dehydrogenase) or an overexpressed dhaKLM operon (encoding dihydroxyacetone kinase subunits KLM);
   a disruption in at least one of a frdA, frdB, frdC, or frdD gene (encoding fumarate reductase); and
   a disruption in a pta gene or a disruption in a poxB gene.

3. An *Escherichia coli* strain comprising:
   an overexpressed gldA gene or an overexpressed dhaKLM operon; and
   a disruption in one or more of a adhE gene, a pta gene, a poxB gene; a frdA gene, afrdB gene, frdC gene, or a frdD gene.

4. A method of culturing bacteria to produce a metabolite, comprising the following steps:
   a. inoculating a culture medium comprising glycerol as a feedstock with a bacteria capable of producing a metabolite, said bacteria being selected from the bacteria of claim 1, and
   b. cultivating said bacteria under microaerobic conditions of ≤20 mg $O_2$/L/h, but not aerobic or anaerobic conditions, in said reactor so as to convert said glycerol into a metabolite, wherein the conversion of glycerol into the metabolite does not consume more reducing equivalents than it produces.

5. The method of claim 4, wherein said bacteria is *E. coli* comprising Δpta, ΔfrdA and overexpressed gldA and dhaKLM.

6. The method of claim 4, wherein said metabolite is selected from the groups consisting of ethanol, lactate, succinate, propionate, alanine, and combinations thereof.

7. The method of claim 4, wherein said metabolite is selected from the groups consisting of ethanol, lactate, propionate, succinate, and combinations thereof.

* * * * *

UNITED STATES PATENT AND TRADEMARK OFFICE
CERTIFICATE OF CORRECTION

| | | |
|---|---|---|
| PATENT NO. | : 8,691,552 B2 | Page 1 of 1 |
| APPLICATION NO. | : 13/126499 | |
| DATED | : April 8, 2014 | |
| INVENTOR(S) | : Gonzalez et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 237 days.

Signed and Sealed this
Twenty-first Day of July, 2015

Michelle K. Lee
*Director of the United States Patent and Trademark Office*